US 6,750,314 B2

(12) United States Patent
Miyamoto et al.

(10) Patent No.: US 6,750,314 B2
(45) Date of Patent: Jun. 15, 2004

(54) PROCESS FOR PRODUCING AN AROMATIC POLYCARBONATE

(75) Inventors: Masaaki Miyamoto, Kitakyushu (JP); Kiyoji Kuma, Kitakyushu (JP); Narutoshi Hyoudou, Kitakyushu (JP); Eiji Fujimoto, Kitakyushu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/396,408

(22) Filed: Mar. 26, 2003

(65) Prior Publication Data
US 2003/0166826 A1 Sep. 4, 2003

Related U.S. Application Data

(63) Continuation of application No. PCT/JP01/08149, filed on Sep. 19, 2001.

(30) Foreign Application Priority Data

Sep. 26, 2000 (JP) ........................................ 2000-292470
Jul. 27, 2001 (JP) ........................................ 2001-227560

(51) Int. Cl.$^7$ .............................................. C08G 64/00
(52) U.S. Cl. .................... 528/196; 264/176.1; 264/219; 528/198
(58) Field of Search .............................. 264/176.1, 219; 528/196, 198

(56) References Cited

U.S. PATENT DOCUMENTS

| 6,166,167 A | 12/2000 | Miyamoto et al. |
| 6,288,205 B1 | 9/2001 | Miyamoto et al. |
| 6,294,641 B1 | 9/2001 | Miyamoto et al. |
| 6,348,613 B2 | 2/2002 | Miyamoto et al. |

FOREIGN PATENT DOCUMENTS

| JP | 2000-53759 | 2/2000 |

*Primary Examiner*—Terressa Boykin
(74) *Attorney, Agent, or Firm*—Oblon, Spivak, McClelland, Maier & Neustadt, P.C.

(57) ABSTRACT

To produce an aromatic polycarbonate excellent in physical properties and hue by a simplified step as compared with a conventional one.

A process for producing an aromatic polycarbonate, which comprises the following steps (1) to (3):

(1) a step of reacting phenol with acetone in the presence of an acid catalyst to convert part of the phenol into bisphenol A, to obtain a bisphenol A/phenol composition,
(2) a step of supplying the bisphenol A/phenol composition held in a molten state in a liquid form to an aromatic polycarbonate production step, and
(3) a step of reacting the bisphenol A and a carbonate material to produce an aromatic polycarbonate.

11 Claims, No Drawings

PROCESS FOR PRODUCING AN AROMATIC POLYCARBONATE

This application is a continuation of PCT/JP01/08149 filed Sep. 19, 2001.

TECHNICAL FIELD

The present invention relates to a production process to obtain an aromatic polycarbonate having an excellent quality more efficiently. More particularly, the present invention relates to a process for producing an aromatic polycarbonate capable of forming a molded product having not only physical properties characteristic to an aromatic polycarbonate but also improved hue, wherein a step of purification of its material bisphenol A is simplified.

BACKGROUND ART

In a production process of an aromatic polycarbonate (hereinafter sometimes referred to simply as a polycarbonate) employing bisphenol A as a material, in order to hold the material bisphenol in a molten state, as the bisphenol A as a single substance has a high melting point (158° C.), a higher temperature has to be employed so as to hold a molten state. However, when the material bisphenol A is held in a molten state at a high temperature for several hours, it starts being colored, and if it is used as the material of the polycarbonate, the color tone of the obtained product tends to be impaired, and the product cannot be used as an ordinary polycarbonate product. Accordingly, the bisphenol A has conventionally been held as a solidified powder as a single substance.

However, the solidified bisphenol A has to be handled as a powder, and various influences have been found such that the powder tends to easily block e.g. a piping of an apparatus, or dissolution in e.g. an aqueous alkali solution may be impaired, depending upon the property. Accordingly, it has been variously devised to maintain a prill shape which is less likely to cause blocking and which is easily dissolved. Even though, it is difficult to continue a continuous operation for one year, and the operation has to be stopped every few months for washing the apparatus such as a conveyer, thus leading to a considerable production loss.

The best means to solve the problem is to subject the bisphenol A to polymerization while holding it in a molten state without solidifying it, however, as mentioned above, the bisphenol A single substance has a high melting point, and a higher temperature has to be employed so as to hold it in a molten state. However, when it is held in a molten state at a high temperature, 4-isopropenyl phenol (compound of the following formula (1)) forms in several hours, the material bisphenol A starts being colored, and a polycarbonate produced employing it as a material has an impaired color tone and does not satisfy essentialities as a product. Accordingly, improvement of heat stability of the bisphenol A as a polycarbonate material has strongly been desired.

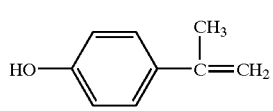

Formula (1)

It is an object of the present invention to provide a process for producing a high quality polycarbonate employing, as a material, bisphenol A having a high purity with suppressed formation of 4-isopropenyl phenol.

Further, another object of the present invention is to provide a process for producing a polycarbonate, which makes it possible to reduce the energy required for conventional cooling for solidification and heating for melting of bisphenol, over the entire process of from production of bisphenol A to production of the polycarbonate.

DISCLOSURE OF THE INVENTION

As mentioned above, a high temperature is required to hold the bisphenol A in a molten state, and holding at a high temperature causes thermal decomposition, thus leading to formation of 4-isopropenyl phenol of the Formula (1) which brings about coloring. Accordingly, it was found that in order to improve heat stability of the material bisphenol A in a molten state, it is most effective to decrease the holding temperature, i.e. to lower the melting point of the bisphenol A.

The present inventors have conducted extensive studies to lower the melting point of the bisphenol A, and as a result, they have found that the composition comprising bisphenol A and phenol has a lower melting temperature than that of bisphenol A single substance, for example, an adduct crystal (hereinafter sometimes referred to simply as "adduct") comprising bisphenol A and phenol in a weight ratio of 7/3 has a melting temperature of 120° C. Further, it was found that when the bisphenol A is held in a molten state as a composition with phenol, it may be held as a melt for several days, and when the bisphenol A thus held in a molten state is used for production of a polycarbonate, a product comparable to a polycarbonate employing a new bisphenol A without being held can be obtained.

Namely, the present invention resides in a process for producing an aromatic polycarbonate, which comprises the following steps (1) to (3):

(1) a step of reacting phenol with acetone in the presence of an acidic catalyst to convert part of the phenol into bisphenol A, to obtain a bisphenol A/phenol composition,
(2) a step of supplying the bisphenol A/phenol composition held in a molten state in a liquid form to an aromatic polycarbonate production step, and
(3) a step of subjecting the bisphenol A and a carbonate material to polymerization to produce an aromatic polycarbonate.

BEST MODE FOR CARRYING OUT THE INVENTION

Now, the present invention will be explained in detail below.

The process for producing an aromatic polycarbonate of the present invention comprises at least (1) a step for producing bisphenol A (2,2-bis(4-hydroxyphenyl)propane), (2) a step of holding the bisphenol A/phenol composition in a molten state, and (3) a step for producing an aromatic polycarbonate.

For production of a high quality aromatic polycarbonate of the present invention, any known process for producing an aromatic polycarbonate from a bisphenol, such as a melt method by means of transesterification of material carbonic acid diester with a bisphenol (transesterification method) or an interfacial method by means of a reaction of a bisphenol with phosgene (phosgene method) may be employed.

The step for producing the bisphenol A as the above step (1) of the present invention is not particularly limited, however, the bisphenol A is produced by reacting phenol with acetone in the presence of an acidic catalyst such as a strongly acidic cation exchange resin, followed by purification, and is obtained as a bisphenol A/phenol composition.

The ratio (molar ratio) of phenol to acetone in the reaction for production of the bisphenol A is usually from 8:1 to 20:1, preferably from 10:1 to 18:1. The reaction temperature is usually from 50 to 90° C.

By the reaction of phenol with acetone, at least part of the phenol is converted to bisphenol A, and as a result, the reaction mixture usually contains bisphenol A, phenol, acetone and water as a by-product.

In the present invention, the bisphenol A/phenol composition is obtained from the above reaction mixture containing bisphenol A by purification with a proper method. As the purification method, for example, a low boiling point substance such as unreacted acetone or water as a by-product is removed, followed by cooling to precipitate an adduct of bisphenol A and phenol in a molar ratio of 1:1 (hereinafter sometimes referred to simply as an adduct), and the crystal is separated from the mother liquor and purified. The adduct after purification as it is, or after prepared to a composition having desired ranges of bisphenol A and phenol by adding phenol thereto or by distilling off part of phenol in the adduct by means of e.g. distillation under reduced pressure, is held in a molten state in a stock tank.

With respect to the proportion of each component in the bisphenol A/phenol composition, bisphenol A/phenol is within a range of from 95/5 to 5/95 (weight ratio). Preferably, bisphenol A/phenol is at most 90/10, more preferably at most 70/30, particularly preferably at most 65/35. Further, it is preferably at least 10/90, more preferably at least 40/60, particularly preferably at least 50/50. If the value of bisphenol A/phenol in the composition is remarkably smaller than the above range (5/95), the productivity of the polycarbonate tends to be low, and if it is remarkably higher than the above range (95/5), the melt temperature of the composition tends to be high, and 4-isopropenyl phenol is likely to form when the composition is held in a molten state.

In such a process for producing bisphenol A, the purity of the bisphenol A to be recovered greatly depends on the purity of its adduct, and a process for producing a high purity adduct is required. Accordingly, a treatment method by means of a series of crystallization steps, comprising plural stages of crystallization steps combined by means of a step of separating the adduct and a step of redissolving it with a high purity phenol between the crystallization steps, has been known. As the bisphenol A used in the present invention, one produced by the above method may be used, and it may optionally be subjected to a crystallization step, and the bisphenol A is not particularly limited.

Impurities derived from the material contained in the bisphenol A or derived from the bisphenol A include bisphenol A derivatives, bisphenol A isomers, chroman type organic compounds and trisphenols, and as typical compounds, compounds of the following Formulae (2) to (5) may be mentioned. As the total content of such impurities, they are usually contained in an amount of from about several hundreds ppm to about 1000 ppm.

Needless to say, the lower the content, the better, however, the quality of the polycarbonate as a normal product can be maintained with a content at a level of several hundreds ppm, in view of the balance between the purification degree and yield.

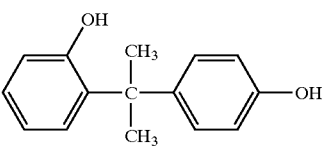

Formula (2)

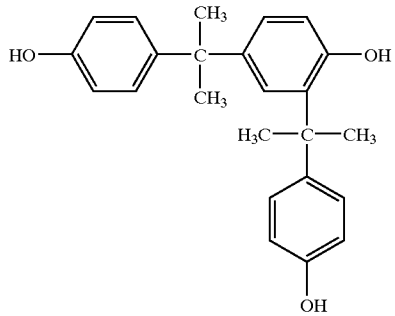

Formula (3)

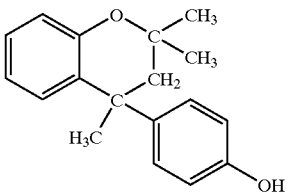

Formula (4)

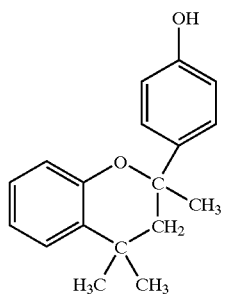

Formula (5)

The total content of the bisphenol A derivatives, bisphenol isomers, chroman type organic compounds and trisphenols as impurities contained in the bisphenol A can be decreased by purification. Among the impurities, one having an unsaturated functional group such as 4-isopropenyl phenol of the above Formula (1) has a great impact on the color tone of the product polycarbonate, and is likely to cause coloring, and accordingly it is preferred to decrease the content as far as possible. However, the compound forms also in a stage where the bisphenol A single substance after purification is held in a molten state, and accordingly the holding conditions of the bisphenol A single substance are extremely important, and attention has to be paid.

The content of 4-isopropenyl phenol is preferably as low as possible, however, if the composition is held in a molten state, it is difficult to make the content zero, and accordingly the content is at most 1000 ppm, preferably at most 500 ppm, furthermore preferably at most about 200 ppm, in such an extent that it does not influence as a monophenol over the molecular weight of the formed polycarbonate, and it does not relate to the side reaction as an olefin.

The step of holding the bisphenol A/phenol composition in a molten state as the above step (2) of the present invention refers to a part of or the entire step from a point where after the above-described bisphenol A is produced, the composition having bisphenol A and phenol adjusted to an appropriate proportion is obtained and is held in a molten state in a liquid form, to a point where said composition is supplied to a polymerization step employing the bisphenol A as a material (step for producing a polycarbonate) in the form of a liquid molten composition.

In the present invention, in order to obtain bisphenol A having a low content of 4-isopropenyl phenol, it is important that the bisphenol A is held in a molten state under specific conditions, i.e., it is held as a composition constituted in a specific compositional ratio with phenol at a predetermined temperature.

With respect to the stable composition (weight ratio) and the holding temperature in holding the bisphenol A in a molten state, bisphenol A/phenol=95/5 to 5/95, and the holding temperature at that time is from 160° C. to 40° C., the more stable composition is from 70/30 to 40/60, and the holding temperature at that time is from 130 to 100° C., and the furthermore stable composition is from 65/35 to 50/50, and the holding temperature at that time is from 120° C. to 105° C. The most preferred composition of bisphenol A/phenol is from 65/35 to 55/45, which is favorable for simplifying the step, and the holding temperature at that time is from 120° C. to 105° C.

The holding temperature is preferably short, since the deterioration reaction rate of the bisphenol A is a function of the temperature and the time. However, a residence of from several hours to several tens hours is inevitable industrially, and it is essential that there is no influence in a time to such an extent. More specifically, when the holding time is from 120° C. to 105° C., it is preferably at most 72 hours, more preferably at most 48 hours, when the holding temperature is from 130° C. to 105° C., it is preferably at most 48 hours, more preferably at most 36 hours, and when the holding temperature is from 160° C. to 105° C., it is preferably at most 36 hours, more preferably at most 24 hours.

The bisphenol A/phenol composition in a molten state is supplied to the succeeding polymerization step by e.g. piping or tanker, as in the form of a liquid without being solidified. The molten composition may directly be supplied to a polymerization reaction apparatus, or it may be supplied to a material preparation tank provided at a stage prior to the polymerization reaction apparatus, preliminarily mixed with e.g. the carbonate material and/or solvent, and supplied to the succeeding polymerization reaction apparatus. Further, although the composition may be used for polymerization as it is, it is preferred to remove phenol by an operation such as distillation under reduced pressure immediately before the polymerization to obtain a melt, most part of which comprises bisphenol A, preferably a melt, at least 99% of which comprises bisphenol A, and to transfer the bisphenol A in a molten state to the material preparation tank to carry out the polymerization step.

In the case where the bisphenol A is transferred to the material preparation tank after phenol in it is removed, the melt temperature increases as the content of the bisphenol A increases, and it is necessary to increase the temperature so as to hold the composition as a melt, and 4-isopropenyl phenol is likely to form at this stage, and accordingly the time for which the bisphenol A is held in a molten state as a single substance is preferably as short as possible, and it is preferably at most 12 hours, more preferably at most 6 hours, particularly preferably at most 4 hours.

With respect to the conditions when said bisphenol A/phenol composition is held in a molten state, needless to say, an environment under an inert gas such as nitrogen is preferred. Particularly, an atmosphere with an oxygen concentration of as low as possible is preferred, and usually use of an atmosphere with an oxygen concentration of at most 0.005 vol %, preferably at most 0.001 vol % is advantageous. As the material of a container, a material at a level of a common austenite type stainless is preferred.

The present invention does not exclude a case where, in the step of holding the bisphenol A/phenol composition in a molten state, the composition is temporarily solidified during the step. For example, even though part of the composition is solidified during transportation by e.g. a tanker, it may be re-melted by heating at a point where it is supplied from the tanker to the succeeding polymerization step. However, reheating after solidification takes energy and time, and accordingly it is preferred that the composition is held in a molten state over substantially entire step of holding the composition in a molten state.

Then, a step for producing a polycarbonate as the above step (3) of the present invention will be explained.

Preferred embodiment of the step for producing a polycarbonate is such that phenol is distilled off from the bisphenol A/phenol composition supplied in a molten state by e.g. distillation under reduced pressure to obtain a melt consisting essentially of bisphenol A, which is subjected to a polymerization reaction.

The phenol content remaining in the bisphenol A is preferably as low as possible, however, it is not particularly required to decrease it to a level of ppm order as in the case where the bisphenol A is solidified to obtain a powder, and it is usually at most several %, preferably at most several thousands ppm, more preferably at most about several hundreds ppm, as a level of not affecting production conditions of the polycarbonate as described hereinafter, and as a level of not affecting the molecular weight of the formed polycarbonate as a monophenol and not affecting the supply ratio with the carbonate material.

As the evaporation apparatus, e.g. a distillation column, a stripping apparatus, a packed tower or a thin-film evaporator may be used, and it is preferred to apply a treatment to remove oxygen from the surface of the apparatus prior to its use. The evaporation apparatus may be used in one stage or in multiple stages. With respect to the operation conditions, as the operation conditions of the one evaporation apparatus in the case of one stage and the final evaporation apparatus in the case of the multiple stages, conditions with a temperature of from 150 to 220° C., preferably from 170 to 200° C., a pressure of at most 100 Torr, preferably at most 40 Torr, and an oxygen concentration in the atmosphere of at most 0.005 vol %, preferably at most 0.001 vol %, are employed. Further, it is also effective to spray steam from the lower part of the evaporator to carry out steam distillation (steam stripping).

The bisphenol A melt obtained by distillation of phenol from said bisphenol A/phenol molten composition is successively mixed with a carbonic acid diester such as diphenyl carbonate (melt method) or mixed with an aqueous alkali solution and phosgene, depending upon the polymerization method to be employed, so as to carry out the following polymerization step.

On the other hand, the distilled phenol after purified as the case requires, may be recycled as the material for production of bisphenol A or may be reused as a material for production of a carbonic acid diester particularly diphenyl carbonate.

In the process for producing a polycarbonate employed in the present invention, a melt method (transesterification method) or an interfacial method (phosgene method) may be employed.

In the process for producing a polycarbonate by the melt method (transesterification method), a carbonic acid diester is used as the carbonate material.

The carbonic acid diester used in the present invention is represented by the following Formula (6).

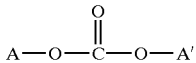

Formula (6)

wherein each of A and A' is a $C_1$–$C_{18}$ aliphatic group which may be substituted or an aromatic group, provided that A and A' may be the same or different.

The carbonic acid diester of the above Formula (6) may, for example, be a dialkyl carbonate such as dimethyl carbonate, diethyl carbonate or di-t-butylcarbonate, or a substituted diphenyl carbonate such as diphenyl carbonate or ditolyl carbonate, and it is preferably diphenyl carbonate or a substituted diphenyl carbonate, particularly preferably diphenyl carbonate. These carbonic acid diesters may be used alone or in combination as a mixture of at least two.

As the process for producing the carbonic acid diester used in the present invention, various production methods have been known, and the method is not particularly limited. For example, a phase interfacial phosgenation reaction of a monohydroxy compound in an aqueous alkali solution, a phosgenation reaction of a monohydroxy compound in the presence of an aromatic heterocyclic basic nitrogen compound or its salt in a catalytic amount, or a transesterification reaction of a dialkyl carbonate and an aromatic monohydroxy compound, may be employed.

To produce an aromatic polycarbonate by the melt method in the present invention, bisphenol A and a carbonic acid diester such as diphenyl carbonate are used, and the diphenyl carbonate is used preferably in an amount of from 1.01 to 1.30 mol, preferably from 1.02 to 1.20 mol, per 1 mol of the bisphenol A.

The bisphenol A in the form of a melt and diphenyl carbonate in this ratio are charged in a material preparation tank and mixed. Such a composition is sufficient to decrease the melting point of the bisphenol A, and it is found that such a composition to be subjected to polymerization decreases the melting point to about 120° C. Accordingly, holding such a mixture in a molten state is considered to be much more superior to holding a single substance.

When an aromatic polycarbonate is produced by the melt method (transesterification method), usually a transesterification catalyst is used. As the transesterification catalyst used in the present invention, an alkali metal compound and/or an alkaline earth metal compound are mainly used, and a basic compound such as a basic boron compound, a basic phosphorus compound, a basic ammonium compound or an amine type compound may be subsidiary used together. These catalysts may be used alone or in combination as a mixture of at least two.

As the catalytic amount, it is used in an amount of from $1\times10^{-9}$ to $1\times10^{-3}$ mol per 1 mol of the bisphenol A, and the alkali metal compound and/or alkaline earth metal compound which are favorable in view of physical properties and handling, are used in an amount of from $1\times10^{-8}$ to $1\times10^{-5}$ mol, preferably from $2\times10^{-8}$ to $8\times10^{-6}$ mol, per 1 mol of the bisphenol A. If the amount is smaller than this, no polymerization activity required for production of a polycarbonate having predetermined molecular weight and terminal hydroxyl group amount can be obtained, and if it is larger than this, the polymer hue tends to be impaired, and the polymer tends to be more branched.

The alkali metal compound may, for example, be sodium hydroxide, potassium hydroxide, lithium hydroxide, cesium hydroxide, sodium hydrogen carbonate, potassium hydrogen carbonate, lithium hydrogen carbonate, cesium hydrogen carbonate, sodium carbonate, potassium carbonate, lithium carbonate, cesium carbonate, sodium acetate, potassium acetate, lithium acetate, cesium acetate, sodium stearate, potassium stearate, lithium stearate, cesium stearate, sodium borohydride, potassium borohydride, lithium borohydride, cesium borohydride, sodium phenylboron, potassium phenylboron, lithium phenylboron, cesium phenylboron, sodium benzoate, potassium benzoate, lithium benzoate, cesium benzoate, disodium hydrogen phosphate, dipotassium hydrogen phosphate, dilithium hydrogen phosphate, dicesium hydrogen phosphate, disodium phenyl phosphate, dipotassium phenyl phosphate, dilithium phenyl phosphate, dicesium phenyl phosphate, an alcoholate of sodium, potassium, lithium or cesium, or a disodium salt, a dipotassium salt, a dilithium salt or a dicesium salt of phenol or bisphenol A.

Further, the alkaline earth metal compound may, for example, be calcium hydroxide, barium hydroxide, magnesium hydroxide, strontium hydroxide, calcium hydrogen carbonate, barium hydrogen carbonate, magnesium hydrogen carbonate, strontium hydrogen carbonate, calcium carbonate, barium carbonate, magnesium carbonate, strontium carbonate, calcium acetate, barium acetate, magnesium acetate, strontium acetate, calcium stearate, barium stearate, magnesium stearate or strontium stearate.

Specific examples of the basic boron compound include hydroxides of e.g. tetramethylboron, tetraethylboron, tetrapropylboron, tetrabutylboron, trimethylethylboron, trimethylbenzylboron, trimethylphenylboron, triethylmethylboron, triethylbenzylboron, triethylphenylboron, tributylbenzylboron, tributylphenylboron, tetraphenylboron, benzyltriphenylboron, methyltriphenylboron and butyltriphenylboron.

The basic phosphorus compound may, for example, be triethylphosphine, tri-n-propylphosphine, triisopropylphosphine, tri-n-butylphosphine, triphenylphosphine, tributylphosphine or a quaternary phosphonium salt.

The basic ammonium compound may, for example, be tetramethylammonium hydroxide, tetraethylammonium hydroxide, tetrapropylammonium hydroxide, tetrabutylammonium hydroxide, trimethylethylammonium hydroxide, trimethylbenzylammonium hydroxide, trimethylphenylammonium hydroxide, triethylmethylammonium hydroxide, triethylbenzylammonium hydroxide, triethylphenylammoniuim hydroxide, tributylbenzylammonium hydroxide, tributylphenylammonium hydroxide, tetraphenylammonium hydroxide, benzyltriphenylammonium hydroxide, methyltriphenylammonium hydroxide or butyltriphenylammonium hydroxide.

The amine type compound may, for example, be 4-aminopyridine, 2-aminopyridine, N,N-dimethyl-4-aminopyridine, 4-diethylaminopyridine, 2-hydroxypyridine, 2-methoxypyridine, 4-methoxypyridine, 2-dimethylaminoimidazole, 2-methoxyimidazole, imidazole, 2-mercaptoimidazole, 2-methylimidazole or aminoquinoline.

The transesterification reaction is carried out usually in a multistage step of at least two stages. Specifically, the first stage reaction is carried out under reduced pressure at a temperature of from 120 to 260° C., preferably from 180 to 240° C. for from 0.1 to 5 hours, preferably from 0.1 to 3 hours. Then, the reaction temperature is increased while increasing the degree of pressure reduction in the reaction system, and finally a polycondensation reaction under a reduced pressure of at most 1 mmHg at a temperature of from 240 to 320° C. is carried out.

The style of the reaction may be any reaction of a batch type, a continuous type or a combination of batch type and continuous type, and the apparatus to be used may be any type of a tank type, a tube type or a tower type. The viscosity-average molecular weight (Mv) of the polycarbonate to be obtained after the polycondensation reaction is usually from about 10,000 to about 100,000.

The monohydroxy compound formed as a by-product in the transesterification reaction, after purified by e.g. distillation as the case requires, may be reused as the material for production of the above carbonic acid diester. In a case where the carbonic acid diester used is diphenyl carbonate, the monohydroxy compound formed as a by-product in the polymerization is phenol, and it may be recycled, after purified by e.g. distillation as the case requires, as a material for production of the carbonic acid diester and as the material for production of bisphenol A as well, for the above step 1).

Then, in the process for producing a polycarbonate by the interfacial method (phosgene method), phosgene is used as the carbonate material.

The interfacial method is usually to react bisphenol A with phosgene in the presence of an inert organic solvent which is a solvent of an acid binding agent such as a hydroxide of an alkali metal or an alkaline earth metal and a polycarbonate formed by the reaction, i.e. in the presence of a condensation catalyst in short. For the reaction, as the case requires, an optional chain terminator and/or a branching agent may be added.

As a suitable chain terminator, various monophenols, for example, normal phenol, $C_1$–$C_{14}$ alkyl phenols such as cumyl phenol, isooctylphenol, p-t-butyl phenol and p-cresol, and halogenated phenols such as p-chlorophenol and 2,4,6-tribromophenol may be mentioned. Particularly, phenol, cumyl phenol, isooctylphenol and p-t-butyl phenol are suitable chain terminators. The amount of the chain terminator varies depending upon the molecular weight of the aimed polycarbonate, but, it is used in an amount of usually from 0.5 to 10 wt % based on the amount of the bisphenol in the aqueous phase.

The branching agent used may be selected from various compounds having three or more functional groups. A suitable branching agent may, for example, be a compound having three or more phenolic hydroxyl groups such as 2,4-bis-(4-hydroxyphenyl-isopropyl)-phenol, 2,6-bis-(2'-hydroxy-5'-methylbenzyl)-4-methylphenol, 2-(4-hydroxyphenyl)-2-(2,4-hydroxyphenyl)-propane or 1,4-bis-(4,4'-dihydroxytriphenylmethyl)-benzene. Further, the compound having three functional groups may, for example, be 2,4-dihydroxybenzoic acid, trimesic acid, cyanuric chloride, bis-(4-hydroxyphenyl)-2-oxo-2,3-dihydroxyindole or 3,3-bis-(4-hydroxy-3-methylphenyl)-2-oxo-2,3-dihydroindole. Among them, a compound having three or more phenolic hydroxy groups is suitable. The amount of the branching agent varies depending upon the aimed degree of branching, but it is used in an amount of usually from 0.05 to 2 mol %, based on the amount of the bisphenol A in the aqueous phase.

The organic phase in the process of the present invention is required to contain an optional inert organic solvent in which phosgene and reaction products such as a carbonate oligomer (hereinafter referred to simply as oligomer) and the polycarbonate are dissolved, but which has no compatibility with water, that is, which does not form a solution with water, at a reaction temperature under a reaction pressure.

A typical inert organic solvent may, for example, be an aliphatic hydrocarbon such as hexane or n-heptane, a chlorinated aliphatic hydrocarbon such as methylene chloride, chloroform, carbon tetrachloride, dichloroethane, trichloroethane, tetrachloroethane, dichloropropane or 1,2-dichloroethylene, an aromatic hydrocarbon such as benzene, toluene or xylene, a chlorinated aromatic hydrocarbon such as chlorobenzene, o-dichlorobenzene or chlorotoluene, or a substituted aromatic hydrocarbon such as nitrobenzene or acetophenone. Among them, a chlorinated hydrocarbon such as methylene chloride or chlorobenzene is particularly preferably used.

These inert organic solvents may be used alone or as a mixture with another solvent.

In a case where chlorobenzene is used alone, in order to obtain a technically useful concentration of the polycarbonate in chlorobenzene, a high operation temperature has to be employed at the time of reaction and washing. Further, a preferred combination of solvents in production of an industrially important polycarbonate comprising bisphenol A as the base is a mixture of methylene chloride with toluene, and it may be used in the process of the present invention as the case requires.

The aqueous phase in the process of the present invention is required to contain at least three components of water, bisphenol A and an alkali metal hydroxide. In the aqueous phase, the bisphenol A reacts with an alkali metal hydroxide such as sodium hydroxide or potassium hydroxide to form a water soluble alkali metal salt. Accordingly, in the material preparation tank, the bisphenol A melt is gradually charged to a preliminarily prepared aqueous solution of an alkali metal to form an alkali metal salt. The molar ratio of the bisphenol A to the alkali metal in the aqueous phase is usually preferably from 1:1.8 to 1:3.5, more preferably from 1:2.0 to 1:3.2. In preparation of such an aqueous solution, it is preferred to employ a temperature of at least 20° C., preferably from 30 to 40° C., however, if it is too high, oxidation of the bisphenol A may take place, and accordingly it is preferred that the preparation is carried out at a minimum temperature required in a nitrogen atmosphere, or a small amount of a reducing agent such as hydrosulfite is added.

In the process of the present invention, a condensation catalyst is supplied when the aqueous phase and the organic phase are contacted with each other, prior to contact with phosgene, however, the condensation catalyst may be supplied at the time of contact with phosgene. The condensation catalyst may optionally be selected from various polycondensation catalysts used for two phase interfacial condensation. A suitable polycondensation catalyst may, for example, be trialkylamine, N-ethylpyrrolidone, N-ethylpiperidine, N-ethylmorpholine, N-isopropylpiperidine or N-isopropylmorpholine, and particularly preferred is triethylamine or N-ethylpiperidine.

The phosgene is used in a liquid state or in a gaseous state. The $Cl_2$ concentration in the material phosgene is at most 10 ppm, preferably at most 5 ppm, more preferably at most 1 ppm. The method of removing $Cl_2$ in the material phosgene may, for example, be $Cl_2$ adsorption removal with e.g. activated carbon or separation removal by means of distillation employing the difference in boiling point, and $Cl_2$ may be removed by either method. However, in the case of removal by distillation, considerable distillation stages are required since the removal order is extremely low, such being disadvantageous, and the adsorption removal is considered to be more advantageous. From the viewpoint of temperature control, the phosgene is preferably in a liquid state, and particularly in the case of adsorption removal, the liquid state is advantageous, and when the phosgene is introduced to the reaction in a liquid state, a reaction pressure under which it can be in a liquid state is selected at each reaction temperature. The preferred amount of the phosgene varies depending upon the reaction conditions, particularly the reaction temperature and the concentration of the bisphenol A alkali metal salt in the aqueous phase, however, the number of mols of the phosgene based on 1 mol of the bisphenol A is usually from 1 to 2, preferably from 1.05 to 1.5. If the ratio is too high, unreacted phosgene tends to increase, and economical efficiency will be extremely poor. On the other hand, if it is too low, CO groups tend to run short, and no appropriate molecular weight elongation will take place, such being unfavorable.

At the stage of obtaining the oligomer, the concentration of the oligomer in the organic phase may be such a range that the obtained oligomer is soluble, and specifically, it is at a level of from 10 to 40 wt %. Further, the proportion of the organic phase is preferably from 0.2 to 1.0 (volume ratio) based on the aqueous solution of the alkali metal salt of bisphenol A i.e. the aqueous phase. The viscosity-average molecular weight (Mv) of the oligomer obtained under such condensation conditions is usually from about 500 to about 10,000, preferably from 1,600 to 4,500, but is not limited to such a molecular weight.

The oligomer thus obtained is formed into a high molecular weight polycarbonate under precondensation conditions in accordance with a conventional method. The polycondensation reaction to make the oligomer have a high molecular weight is carried out preferably by the following embodiment. First, the organic phase in which the oligomer is dissolved is separated from the aqueous phase, and as the case requires, the above-described inert organic solvent is added thereto to adjust the concentration of said oligomer. Namely, the amount of the solvent is adjusted so that the concentration of the polycarbonate in the organic phase obtained after the polycondensation reaction will be from 5 to 30 wt %. Then, an aqueous phase comprising water and an alkali metal hydroxide is newly added, and preferably the above-described condensation catalyst is added thereto so as to adjust the polycondensation conditions, and a predetermined polycondensation is completed in accordance with the two phase interfacial condensation method. The proportion of the organic phase to the aqueous phase at the time of polycondensation is preferably such that the organic phase:aqueous phase is at a level of from 1:0.2 to 1 by the volume ratio.

After completion of the polycondensation, the organic phase is subjected to a washing treatment with an alkali such as NaOH until the remaining chloroformate group is at most 0.01 μeq/g. Then, the organic phase is further washed until the electrolyte disappears, and finally the inert organic solvent is optionally removed from the organic phase to separate the polycarbonate. The viscosity-average molecular weight (Mv) of the polycarbonate thus obtained is usually from about 10,000 to about 100,000.

In the present specification, the viscosity-average molecular weight (Mv) is a value calculated from the following formulae from the relative viscosity ($\eta sp$) measured by means of a Ubbellohde viscometer at a temperature of 20° C. using a methylene chloride solution having a concentration (C) of the oligomer or polycarbonate of 0.6 g/dl.

$$\eta sp/C = [\eta](1+0.28\eta sp) \quad [\eta] = 1.23 \times 10^{-4}(Mv)^{0.83}$$

To the aromatic polycarbonate obtained by the process of the present invention, various additives such as a stabilizer, a releasing agent, a delayer, an antistatic agent, a bulking agent, fibers and an impact strength modifying agent in their effective amounts may be added during separation of the aromatic polycarbonate from the reactor, before processing it or during the process.

The high quality aromatic polycarbonate obtained by the process of the present invention usually has a viscosity-average molecular weight (Mv) of from 10,000 to 100,000 and having remarkably improved heat stability in a high temperature molding, and accordingly its molded product not only has excellent physical properties characteristic to the polycarbonate but also excellent characteristics with less coloring. Accordingly, the polycarbonate of the present invention has such an advantage that the range of its application can significantly be increased as compared with a conventional one.

The aromatic polycarbonate of the present invention may be formed, due to its excellent characteristics, into various molded products such as a film, a thread and a plate, by e.g. injection molding or extrusion. Further, it may be used in various technical fields such as electrical components and building industry, and as a material for lighting equipment and a material for optical apparatus, particularly as a housing of light, an optical lens, an optical disk, an audio disk, etc.

EXAMPLES

Now, the present invention will be explained in further detail with reference to Examples, however, the present invention is by no means restricted to such Examples, unless they exceed the gist of the invention.

% and part(s) in Examples represent wt % and parts by weight unless otherwise specified. Physical properties of the aromatic polycarbonate obtained in the following Examples were measured as follows.
(1) Color tone (YI):
Formation of Sample Plates Polycarbonate pellets obtained in Examples were plasticized at 360° C. by using an injection machine (manufactured by Japan Steel Works, Ltd., trade name JSW J75EII), and then made to stay in a cylinder for 180 seconds to prepare sample plates of 60 mm square with a thickness of 3.2 mm. YI of each of the sample plate at each of the first shot and the tenth shot in the molding was measured, and the difference ($\Delta$YI) was taken as the scale of the thermal stability.
Measurement of the Color Tone With respect to each of the above sample plates, the color tone (YI value) was measured by using a color difference meter (manufactured by Minolta Co., Ltd., trade name CM-3700D). Of the measured value, a small YI value at the first shot indicates that the color tone at the time of stationary molding is favorable, and a small difference in the YI value ($\Delta$YI) between at the first shot and at the tenth shot means that the heat stability at a high temperature is favorable.
(2) Quantitative Analysis of Bisphenol A Derivative, Bisphenol A Isomer, Chroman Type Organic Compound and Trisphenol I Contained in Bisphenol A Measurement was carried out by means of high performance liquid chromatography using as a column μ-Bondasphere manufactured by Waters.
(3) Degree of branching (MIR value)

The degree of branching of the polycarbonate was calculated from the ratio of MI (260° C.) at a load of 21.6 kg to MI (260° C.) at a load of 2.16 kg.

$$MIR = [MI(260/21.6)/MI(260/2.16)]$$

Example 1

Preparation of Bisphenol A

Phenol and acetone were passed through a column type reactor in which an ion exchange resin having a sulfonic group packed, in a molar ratio of phenol/acetone of 13, and a reaction solution of bisphenol A was obtained with 95% of conversion of acetone by a reaction at an inlet temperature of 55° C. and an outlet temperature of 75° C. Then, the above reaction solution was subjected to distillation to remove low boiling point substances such as unreacted acetone and water as a by-product, followed by crystallization at 50° C. by means of external intercooling to obtain a slurry containing an adduct crystal (adduct) comprising bisphenol A and phenol. The crystal adduct slurry was subjected to filtration under reduced pressure by means of a filter having a filter cloth with an aperture of 106 µm set thereto, while keeping the slurry temperature at 50° C., and the obtained crystal adduct cake was washed with refined phenol. The finally obtained adduct was a mixture with a composition of bisphenol A/phenol=7/3 (weight ratio). Impurities in the adduct at this stage were 2,4-bisphenol A=84 ppm, chroman-1=5 ppm and trisphenol=30 ppm, and no 4-isopropenyl phenol was detected. In order to hold the adduct in a molten state in a stock tank (made of SUS316) under conditions of the temperature and time as identified in Table 1, phenol was added to obtain a composition adjusted to have the composition as identified in Table 1. Then, the composition was held in a molten state under normal pressure under nitrogen sealing under conditions as identified in Table 1, and then the content of 4-isopropenyl phenol (IPP) contained in the composition was measured. The results are shown in Table 1.

Transesterification Polycondensation Reaction

The composition (bisphenol A/phenol=50/50: weight ratio) after held in a molten state obtained as mentioned above, with a purpose of subjecting it to polymerization, was subjected to continuous distillation under reduced pressure by using three centrifugal thin-film evaporators (190° C., the degree of pressure reduction was set so that the final residual phenol would be at most 100 ppm) to remove phenol until its content became at most 100 ppm, whereby a bisphenol A melt was obtained, which was immediately charged in a material preparation tank, mixed with diphenol carbonate (1/1.07: molar ratio) and held at 130° C.

To the mixed melt, 1 ml of 0.01N sodium hydroxide (1 µmol based on 1 mol of bisphenol A) as a catalyst was charged in nitrogen, and a polycondensation reaction was carried out at 210° C. under 100 mmHg for 60 minutes, at 240° C. under 15 mmHg for 60 minutes and at 280° C. under 0.5 mmHg for 2 hours, while occasionally removing phenol formed as a by-product, whereby an aromatic polycarbonate having a viscosity-average molecular weight of 20,000 was obtained, which was cut by a cutter to obtain pellets. Using the pellets, a sample plate was formed by the above method to measure the color tone.

Further, the degree of branching (MIR value) at 260° C. was measured. A higher MIR value represents a stronger non-Newtonian flow, and indicates that the branching proceeded. The results are shown in Table 1.

Examples 2 to 6

A polycarbonate was produced in the same manner as in Example 1 except that regarding the composition of bisphenol A and phenol (60/40: weight ratio) adjusted in the same manner as in the above Example 1, the bisphenol A/phenol in a constant proportion as identified in Table 1 was held with different holding temperature and time. The results are shown in Table 1.

Examples 7 to 10

A polycarbonate was produced in the same manner as in Example 1 except that regarding the composition of bisphenol A and phenol, a composition having a proportion of bisphenol A/phenol as identified in Table 1, obtained by controlling the composition adjusting conditions (such as addition or distillation of phenol) as shown in the above Example 1, was held in a constant holding time at a different holding temperature. The results are shown in Table 1.

Example 11

The phenol obtained by distillation at the time of polymerization in the above Example 1 was continuously distilled off under the following conditions to obtain purified phenol.

First stage distillation (low-boiling cutting): 200 Torr, reflux ratio: 3, number of theoretical plates: 4 Second stage distillation (high-boiling cutting): 25 Torr, reflux ratio: 0.3, number of theoretical plates: 4 Using the obtained purified phenol, diphenyl carbonate was produced under the following conditions.

While continuously supplying each of 716 g/hr of the above purified phenol and 30 g/hr of pyridine to a first reactor, the temperature was increased to 150° C. Phosgene (361 g/hr) in a molar ratio of 0.48 based on the supplied phenol was continuously supplied to the first reactor with adequate stirring. The reaction mixture which ran out from the first reactor was supplied to a second reactor through an overflow tube, and the reaction mixture which ran out from the second reactor was similarly supplied to a third reactor. The reaction mixture which ran out from the third reactor was drawn to a polypropylene receiver. A blowing tube of nitrogen gas was installed on the third reactor, and 70 Nl/hr of nitrogen gas was continuously supplied to the reaction mixture.

1 kg of the reaction mixture (composition: diphenyl carbonate 89 wt %, phenol 6 wt %, pyridine hydrochloride 5 wt %, phenylchloroformate undetected) drawn out after the composition was adequately stabilized, was put in a jacketed glass reactor connected to an oil circulating type external heating apparatus, and heated to 85° C. 372 g of an aqueous sodium hydroxide solution having a concentration of 5 wt %, heated at 85° C., was added thereto, followed by stirring for 5 minutes, and after the mixture was left to stand for 30 minutes, the aqueous phase and the organic phase were separately drawn out. The pH after addition of the aqueous sodium hydroxide solution was 9. The drawn out organic phase was put in the jacketed glass reactor connected to an oil circulating type external heating apparatus again, and heated to 85° C. 300 g of demineralized water heated at 85° C. was added thereto, followed by stirring for 5 minutes, and after the mixture was left to stand for 5 minutes, the aqueous phase and the organic phase were separately drawn out.

The separated organic phase was purified by distillation by means of a vacuum distillation column made of SUS304, having 15 Sumitomo/Throuzer lab packings (manufactured by Sumitomo Heavy Industries, Ltd.) packed therein. In particular, free pyridine and phenol were distilled off under distillation conditions with a degree of vacuum of from 10 to 20 Torr, at a reboiler temperature of about 180° C. with a reflux ratio of 1, and then 750 g of purified diphenyl carbonate was obtained under distillation conditions with a degree of vacuum of 10 Torr, at a reboiler temperature of about 180° C. in a reflux ratio of 0.5.

The same operation as in Example 1 was carried out except that the diphenyl carbonate obtained by the above procedure was used instead of the diphenyl carbonate used in Example 1 to produce an aromatic polycarbonate. The quality of the obtained polycarbonate was comparable to that of Example 1.

Example 12

The phenol obtained by distillation at the time of polymerization in the above Example 1 was continuously distilled off under the following conditions to obtain purified phenol.

First stage distillation (low-boiling cutting): 200 Torr, reflux ratio: 3, number of theoretical plates: 4

Second stage distillation (high-boiling cutting): 25 Torr, reflux ratio: 0.3, number of theoretical plates: 4

Using the obtained purified phenol, bisphenol A was prepared. Namely, the same operation as in Example 1 was carried out except that the purified phenol obtained by the above procedure was used instead of the phenol used for "preparation of bisphenol A" in Example 1, to produce an aromatic polycarbonate. The quality of the obtained polycarbonate was comparable to that of Example 1.

Example 13
Interfacial Polycondensation Reaction

A mixture of the composition (bisphenol A/phenol=50/50: weight ratio) obtained in Example 1 after held in a molten state, with a purpose of subjecting it to polymerization, was subjected to continuous distillation under reduced pressure (190° C., the degree of pressure reduction was set so that the final residual phenol would be at most 100 ppm) by using three centrifugal thin-film evaporators to remove phenol until its content became at most 100 ppm, whereby a bisphenol A melt was obtained, and feeding to a material preparation tank at 16.31 kg/hr was immediately started. At the same time, 5.93 kg/hr of sodium hydroxide and 101.1 kg/hr of water were dissolved in the material preparation tank in the presence of 0.018 kg/hr of hydrosulfite, followed by cooling to 25° C. Each of the aqueous phase and an organic phase of 68.0 kg/hr of methylene chloride cooled at 5° C. was supplied to a stainless piping having an inner diameter of 6 mm and an outer diameter of 8 mm, mixed in the piping, and emulsified by using a homomixer (manufactured by TOKUSHU KIKA KOGYO CO., LTD., trade name TK Homomic Lineflow LF-500 type) to prepare an emulsion.

The emulsion of the aqueous solution (aqueous phase) of bisphenol A sodium salt (hereinafter sometimes referred to as "BPA-Na") and methylene chloride (organic phase) thus obtained was drawn out by a piping having an inner diameter of 6 mm and an outer diameter of 8 mm, branched from the homomixer, and in a Teflon pipe reactor having an inner diameter of 6 mm and a length of 34 m, connected to the piping, the emulsion was contacted with a liquid phosgene in an amount of 7.38 kg/hr supplied from a pipe cooled at 0° C., which was separately introduced to the reactor. The liquid phosgene was one purified by such a treatment that the liquid phosgene was passed through a cylindrical container having a diameter of 55 mm and a height of 500 mm, in which activated carbon (Yashicoal S, manufactured by Taihei Kagaku K.K.) having a particle size at a level of from 30 to 60 mesh, a true density of 2.1 g/cc, a porosity of 40%, a specific surface area of 1200 m$^2$/g and a pore volume of 0.86 cc/g was packed, at −5° C. with SV=3.

The above emulsion was subjected to phosgenation and oligomerization while it was passed through the pipe reactor at a linear velocity of 1.7 m/sec for 20 seconds with phosgene. At this time, the reaction temperature was adjusted to be 60° C. in each reaction, and external intercooling to 35° C. was carried out before the emulsion was put in the successive oligomerization tank.

The oligomerized emulsion obtained from the pipe reactor was further introduced to a reaction tank having an internal capacity of 50 l equipped with a stirrer, and stirred in an atmosphere of nitrogen gas at 30° C. for oligomerization so that unreacted BPA-Na present in the aqueous phase was completely consumed, and then the aqueous phase and the organic phase were separated by leaving the emulsion to stand, whereby a methylene chloride solution of the oligomer was obtained. For the oligomerization, each of 0.005 kg/hr of catalyst triethylamine and 0.65 kg/hr of p-t-butyl phenol as a molecular weight modifier was introduced to the oligomerization tank to obtain an oligomer having a chloroformate concentration of 0.36N.

23 kg of the above methylene chloride solution of the oligomer was introduced in a reaction tank having an internal capacity of 70 l equipped with a Faudler blade, and 10 kg of methylene chloride for dilution was added thereto, and further, 1.8 kg of a 25 wt % aqueous sodium hydroxide solution, 6 kg of water and 2.2 g of triethylamine were added thereto, followed by stirring in an atmosphere of nitrogen gas at 30° C. to carry out a polycondensation reaction for 60 minutes to obtain a polycarbonate.

To the reaction solution, 30 kg of methylene chloride and 7 kg of water were added, followed by stirring for 20 minutes, and then stirring was stopped, and the aqueous phase and the organic phase were separated. To the separated organic phase, 20 kg of 0.1N hydrochloric acid was added, followed by stirring for 15 minutes, triethylamine and an alkali component remaining in a small amount were extracted therefrom, stirring was stopped, and the aqueous phase and the organic phase were separated. Further, to the separated organic phase, 20 kg of pure water was added, followed by stirring for 15 minutes, then stirring was stopped, and the aqueous phase and the organic phase were separated. This operation was repeatedly carried out (3 times) until no chlorine ion was detected in the extracted effluent.

The obtained purified polycarbonate solution was powdered by a kneader, followed by drying to obtain a granular powder (flakes). The IPP concentration in the flakes was measured, whereupon the residual amount was 20 ppm, and a normal polycarbonate with Mv=15,000 was obtained.

Comparative Examples 1 to 3

A polycarbonate was produced in the same manner as in Example 1 except that bisphenol A single substance was used instead of the bisphenol A/phenol composition, and the holding temperature and the holding time were changed. The results are shown in Table 1.

Comparative Example 4

In Example 1, phenol was distilled off from the mixture with a composition bisphenol A/phenol=50/50 (weight ratio), and then bisphenol A in the form of a powder air-cooled with a prill column was obtained. A large amount of dust was formed at a stage where the obtained powder bisphenol A was added to the material preparation tank, and even at a stage where said tank was replaced with nitrogen under reduced pressure, various troubles such as blocking of the vacuum line took place. Then, molten diphenyl carbonate was charged to carry out an operation of heating to 150° C., and polymerization operation was carried out in the same manner as in Example 1, however, no elongation to a predetermined molecular weight was carried out, and equilibrium state was achieved at Mv=13,000. This is estimated to be because the charged bisphenol A was blown as a powder. It is found that in a case where the bisphenol A is used as a conventionally employed powder, a special device is required in operation, and a calorimetric loss is significant.

Comparative Example 5

The same operation as in Example 13 was carried out except that the bisphenol A held in a molten state under the conditions of Comparative Example 1 was used to produced a polycarbonate. The IPP concentration in the resulting flakes was so low as 50 ppm, however, only one having a molecular weight Mv=9,000 was obtained, and it is found that the most of IPP acted as a molecular terminal terminator.

(1) a step of reacting phenol with acetone in the presence of an acid catalyst to convert part of the phenol into bisphenol A, to obtain a bisphenol A/phenol composition, (2) a step of supplying the bisphenol A/phenol composition held in a molten state in a liquid form to an aromatic polycarbonate production step, and (3) a step of subjecting the bisphenol A and a carbonate material to polymerization to produce an aromatic polycarbonate.

2. The process for producing an aromatic polycarbonate according to claim 1, wherein the carbonate material is a carbonic acid diester or phosgene.

3. The process for producing an aromatic polycarbonate according to claim 2, wherein a monohydroxy compound formed as a by-product when the carbonic acid diester and the bisphenol A are subjected to polymerization to produce

TABLE 1

| | Composition (BPA/PHOH) | Temperature (° C.) | Time (hr) | IPP formation amount (ppm) | Initial YI | ΔYI | MIR value |
|---|---|---|---|---|---|---|---|
| Example 1 | 50/50 | 110 | 580 | 100 | 1.76 | 0.52 | 12.5 |
| Example 2 | 60/40 | 120 | 340 | 100 | 1.80 | 0.45 | 12.7 |
| Example 3 | 60/40 | 130 | 200 | 100 | 1.82 | 0.40 | 13.1 |
| Example 4 | 60/40 | 140 | 120 | 100 | 1.72 | 0.48 | 13.3 |
| Example 5 | 60/40 | 150 | 80 | 100 | 1.77 | 0.51 | 12.3 |
| Example 6 | 60/40 | 160 | 50 | 100 | 1.83 | 0.60 | 12.0 |
| Example 7 | 95/5 | 160 | 300 | 840 | 2.21 | 0.55 | 14.6 |
| Example 8 | 90/10 | 155 | 300 | 630 | 2.01 | 0.53 | 14.4 |
| Example 9 | 80/20 | 140 | 300 | 300 | 1.95 | 0.50 | 13.9 |
| Example 10 | 60/40 | 110 | 300 | 60 | 1.65 | 0.37 | 12.1 |
| Comparative Example 1 | 100/0 | 160 | 300 | 2.14% | No normal Mv up | — | |
| Comparative Example 2 | 100/0 | 170 | 300 | 4.34% | No normal Mv up | — | — |
| Comparative Example 3 | 100/0 | 160 | 50 | 3500 ppm | 3.86 | 1.06 | 21.6 |

Note:
BPA Bisphenol A
PHOH Phenol
IPP 4-Isopropenyl phenol

INDUSTRIAL APPLICABILITY

According to the process for producing an aromatic polycarbonate of the present invention, a polycarbonate can be obtained from a high purity material bisphenol A, and its molded product has excellent physical properties characteristic to a polycarbonate and is also excellent in hue, and accordingly it can be applied to a wide range of applications. Further, in the process for producing an aromatic polycarbonate of the present invention, the step of purification of the material bisphenol A can be simplified, and accordingly the process is a production process excellent in economical efficiency, and is industrially advantageous.

The entire disclosures of Japanese Patent Application No. 2000-292470 filed on Sep. 26, 2000 and Japanese Patent Application No. 2001-227560 filed on Jul. 27, 2001 including specifications, claims and summaries are incorporated herein by reference in their entireties.

What is claimed is:

1. A process for producing an aromatic polycarbonate, which comprises the following steps (1) to (3):

an aromatic polycarbonate, is reused as a material for production of the carbonic acid diester.

4. The process for producing an aromatic polycarbonate according to claim 1, wherein diphenyl carbonate is used as the carbonic acid diester as the carbonate material, and phenol formed as a by-product in the above step (3) of subjecting the carbonate material and the bisphenol A to polymerization to produce an aromatic polycarbonate, is recycled for the above step (1) as a material for production of the bisphenol A.

5. The process for producing an aromatic polycarbonate according to claim 1, wherein the bisphenol A/phenol composition held in a molten state in a liquid form has a proportion of bisphenol A/phenol of from 95/5 to 5/95 (weight ratio).

6. The process for producing an aromatic polycarbonate according to claim 1, wherein phenol is removed from the bisphenol A/phenol composition held in a molten state in a liquid form to isolate the bisphenol A, and then the bisphenol A and the carbonate material are subjected to polymerization.

7. The process for producing an aromatic polycarbonate according to claim 1, wherein the 4-isopropenyl phenol content in the bisphenol A to be subjected to polymerization is less than 1000 ppm.

8. The process for producing an aromatic polycarbonate according to claim 1, wherein the bisphenol A/phenol composition is held in a molten state in a liquid form at 160° C. or below.

9. The process for producing an aromatic polycarbonate according to claim 8, wherein the bisphenol A/phenol composition is held in a molten state in a liquid form at 40° C. or above.

10. The process for producing an aromatic polycarbonate according to claim 1, wherein the carbonate material is a carbonic acid diester, and the polymerization of the bisphenol A and the carbonic acid diester is carried out by a molten method.

11. The process for producing an aromatic polycarbonate according to claim 1, wherein the carbonate material is phosgene, and the polymerization of the bisphenol A and the phosgene is carried out by an interfacial method.

* * * * *